United States Patent [19]
Yoshitake et al.

[11] Patent Number: 5,936,110
[45] Date of Patent: Aug. 10, 1999

[54] SILATRANE DERIVATIVE AND CURABLE SILICONE COMPOSITION CONTAINING SAME

[75] Inventors: Makoto Yoshitake; Masayuki Onishi, both of Chiba Prefecture, Japan

[73] Assignee: Dow Corning Toray Silicone Co., Ltd., Tokyo, Japan

[21] Appl. No.: 09/172,797

[22] Filed: Oct. 14, 1998

[30] Foreign Application Priority Data

Oct. 13, 1997 [JP] Japan ...................................... 9-294912
Nov. 28, 1997 [JP] Japan ...................................... 9-344296

[51] Int. Cl.⁶ ................................. C07F 7/08; C07F 7/10
[52] U.S. Cl. ............................ 556/408; 528/15; 528/31; 528/32; 528/33
[58] Field of Search .............................. 556/408; 528/15, 528/31, 32, 33

[56] References Cited

U.S. PATENT DOCUMENTS

| | | | |
|---|---|---|---|
| 2,953,545 | 9/1960 | Finestone | 260/47 |
| 3,032,576 | 5/1962 | Morehouse | 556/408 |
| 3,118,921 | 1/1964 | Samour | 556/408 |
| 3,133,108 | 5/1964 | Finestone | 556/408 |
| 4,048,206 | 9/1977 | Voronkov et al. | 556/405 |
| 4,072,701 | 2/1978 | Pletka et al. | 556/413 |
| 4,129,585 | 12/1978 | Buder et al. | 556/428 |

FOREIGN PATENT DOCUMENTS

| | | |
|---|---|---|
| 53-31689 | 3/1978 | Japan . |
| 52-8854 | 9/1979 | Japan . |
| 61-69781 | 4/1986 | Japan . |
| 55-41702 | 8/1994 | Japan . |
| 7-113083 | 5/1995 | Japan . |
| 5-32397 | 6/1996 | Japan . |

*Primary Examiner*—Paul F. Shaver
*Attorney, Agent, or Firm*—Larry A. Milco

[57] ABSTRACT

A silatrane derivative having the formula:

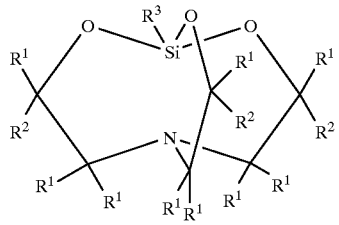

wherein each $R^1$ is independently a hydrogen atom or an alkyl group; each $R^2$ is independently selected from the group consisting of a hydrogen atom, an alkyl group, and an alkoxysilyl-containing organic group having the general formula:

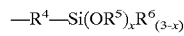

wherein $R^4$ is a divalent organic group, $R^5$ is a $C_1$ to $C_{10}$ alkyl group, $R^6$ is a monovalent hydrocarbon group, and x is 1, 2, or 3, with the proviso that at least one $R^2$ is the alkoxysilyl-containing organic group; and each $R^3$ is independently selected from the group consisting of a monovalent hydrocarbon group, a $C_1$ to $C_{10}$ alkoxy group, a glycidoxyalkyl group, an oxiranylalkyl group, an acyloxyalkyl group, a haloalkyl group, and an aminoalkyl group.

24 Claims, No Drawings

SILATRANE DERIVATIVE AND CURABLE SILICONE COMPOSITION CONTAINING SAME

FIELD OF THE INVENTION

The present invention relates to a silatrane derivative, and more particularly to a silatrane derivative having at least one alkoxysilyl-containing organic group and to a method for the preparation thereof. The present invention further relates to an adhesion promoter comprising a silatrane derivative and to a curable silicone composition containing same.

BACKGROUND OF THE INVENTION

Compositions composed of a reaction mixture of an aminoalkylalkoxysilane and an epoxyalkylalkoxysilane (see Japanese Patent Publications 52-8854, 55-41702, and 7-113083), and compositions composed of a cyclic aminoalkylsilane (see Japanese Patent Publication 5-32397) have been proposed as adhesion promoters which enhance the adhesion of curable silicone compositions. However, these adhesion promoters were not capable of imparting sufficient adhesion to a curable silicone composition.

Meanwhile, there are known silatrane compounds expressed by the following formula, in which R is a methyl group, phenyl group, methoxy group, or ethoxy group, but good adhesion was still not exhibited when one of these silatrane compounds was added to a curable silicone composition.

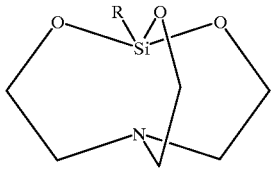

SUMMARY OF THE INVENTION

The inventors arrived at the present invention as a result of research they conducted in an effort to solve the above problem.

Specifically, an object of the present invention is to provide a silatrane derivative and a curable silicone composition that contains the silatrane derivative and exhibits good adhesion.

The present invention is directed to a silatrane derivative having the formula:

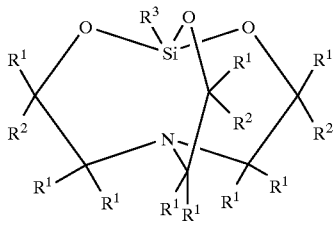

wherein each $R^1$ is independently a hydrogen atom or an alkyl group; each $R^2$ is independently selected from the group consisting of a hydrogen atom, an alkyl group, and an alkoxysilyl-containing organic group having the general formula:

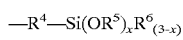

wherein $R^4$ is a divalent organic group, $R^5$ is a $C_1$ to $C_{10}$ alkyl group, $R^6$ is a substituted or unsubstituted monovalent hydrocarbon group, and x is 1, 2, or 3, with the proviso that at least one $R^2$ group is the alkoxysilyl-containing organic group; and each $R^3$ is independently selected from the group consisting of a substituted or unsubstituted monovalent hydrocarbon group, a $C_1$ to $C_{10}$ alkoxy group, a glycidoxyalkyl group, an oxiranylalkyl group, an acyloxyalkyl group, a haloalkyl group, and an aminoalkyl group.

The present invention is also directed to a method of preparing a silatrane derivative. The instant invention is further directed to an adhesion promoter comprising a silatrane derivative and to a curable silicone composition containing same.

DETAILED DESCRIPTION OF THE INVENTION

First, the silatrane derivative of the present invention will be described in detail. The silatrane derivative of the present invention is expressed by the general formula:

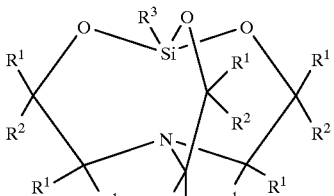

In the above formula, each $R^1$ is independently a hydrogen atom or an alkyl group. Examples of the alkyl group of $R^1$ include methyl, ethyl, propyl, butyl, pentyl, isopropyl, isobutyl, cyclopentyl, and cyclohexyl. It is particularly preferred for $R^1$ to be a hydrogen atom or a methyl group. Each $R^2$ in the above formula is independently selected from the group consisting of a hydrogen atom, an alkyl group, and an alkoxysilyl-containing organic group expressed by the general formula:

with the proviso that at least one $R^2$ group is the alkoxysilyl-containing organic group. Examples of the alkyl group of $R^2$ are the same as the alkyl groups listed for $R^1$ above. For the alkoxysilyl-containing organic group of $R^2$, $R^4$ in the formula is a divalent organic group, examples of which include methylene, ethylene, methylmethylene, propylene, methylethylene, butylene, hexylene, 1-methylpentylene, 1,4-dimethylbutylene, and other alkylene groups; and methyleneoxypropylene, methyleneoxypentylene, and other alkyleneoxyalkylene groups; with ethylene, propylene, butylene, methyleneoxypropylene, and methyleneoxypentylene being preferable. $R^5$ in the formula is a $C_1$ to $C_{10}$ alkyl group, examples of which include the same alkyl groups as given above for $R^1$, with a methyl group or ethyl group being preferable. $R^6$ in the formula is a substituted or unsubstituted monovalent hydrocarbon group, examples of which include a methyl group, ethyl group, propyl group, butyl group, pentyl group, isopropyl group, isobutyl group, cyclopentyl group, cyclohexyl group, and other alkyl groups; a phenyl group, tolyl group, xylyl group, naphthyl group, and other aryl groups; a vinyl group, allyl group, butenyl group, pentenyl group, hexenyl group, and other alkenyl groups; a benzyl group, phenethyl group, and other aralkyl groups; and a chloromethyl group, 3-chloropropyl group, 3,3,3-trifluoropropyl group, nonafluorobutylethyl group, and other halogenated alkyl groups, with a methyl group being preferable. x in the formula is 1, 2, or 3, with 3 being preferable.

The following groups are examples of the alkoxysilyl-containing organic group of $R^2$:

—$(CH_2)_2Si(OCH_3)_3$,
—$(CH_2)_2Si(OCH_3)_2CH_3$,
—$(CH_2)_3Si(OC_2H_5)_3$,
—$(CH_2)_3Si(OC_2H_5)(CH_3)_2$,
—$(CH_2O(CH_2)_3Si(OCH_3)_3$,
—$(CH_2O(CH_2)_3Si(OC_2H_5)_3$,
—$CH_2O(CH_2)_3Si(OCH_3)_2CH_3$,
—$CH_2O(CH_2)_3Si(OC_2H_5)_2CH_3$,
—$CH_2OCH_2Si(OCH_3)_3$, and
—$CH_2OCH_2Si(OCH_3)(CH_3)_2$.

$R^3$ in the above formula is at least one type of group selected from the group consisting of substituted or unsubstituted monovalent hydrocarbon groups, $C_1$ to $C_{10}$ alkoxy groups, glycidoxyalkyl groups, oxiranylalkyl groups, acyloxyalkyl groups, haloalkyl groups, and aminoalkyl groups. Examples of the monovalent hydrocarbon group of $R^3$ are the same as the monovalent hydrocarbon groups listed for $R^6$ above; examples of the alkoxy group of $R^3$ include a methoxy group, ethoxy group, and propoxy group; examples of the glycidoxyalkyl group of $R^3$ include a 3-glycidoxypropyl group; examples of the oxiranylalkyl group or $R^3$ include a 4-oxiranylbutyl group and an 8-oxiranyloctyl group; examples of the acyloxyalkyl group of $R^3$ include an acetoxypropyl group and a 3-methacryloxypropyl group; and examples of the aminoalkyl group of $R^3$ include a 3-aminopropyl group and an N-(2-aminoethyl)-3-aminopropyl group.

The following compounds are examples of silatrane derivatives according to the present invention:

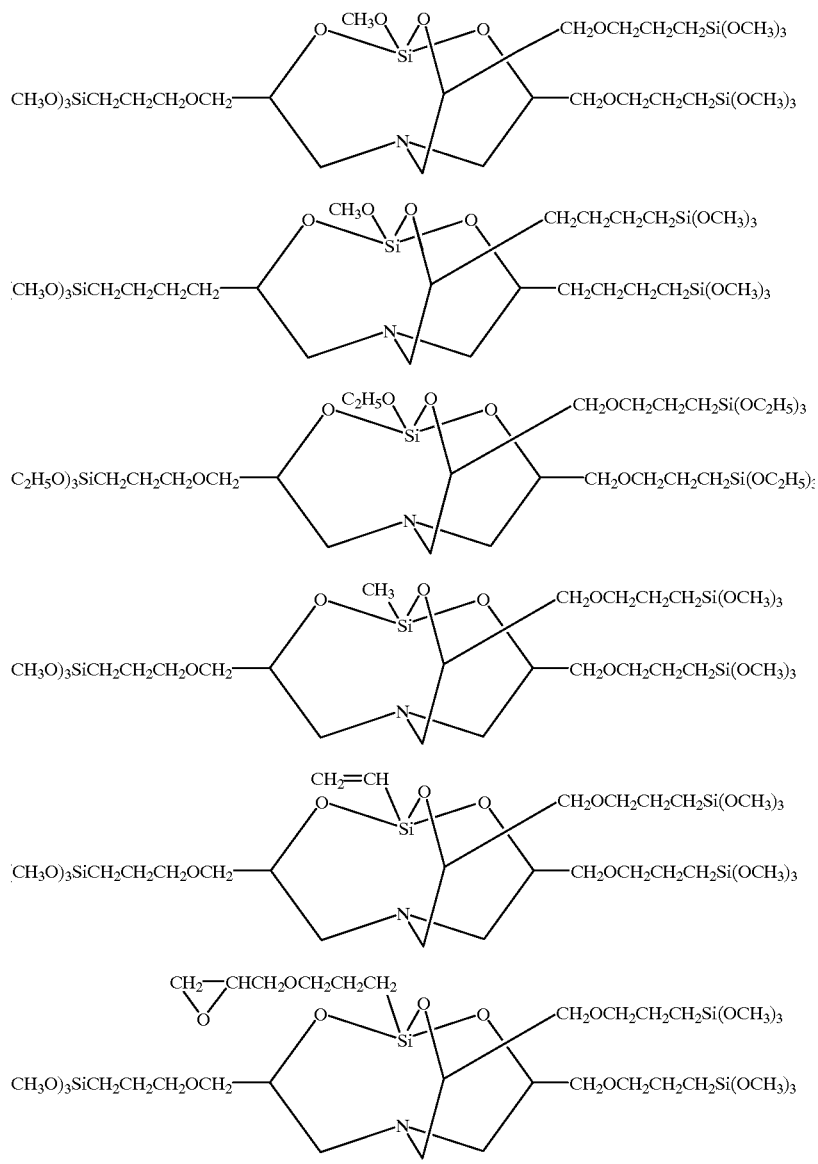

-continued
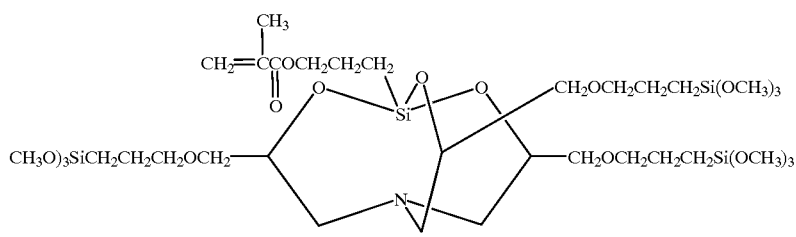
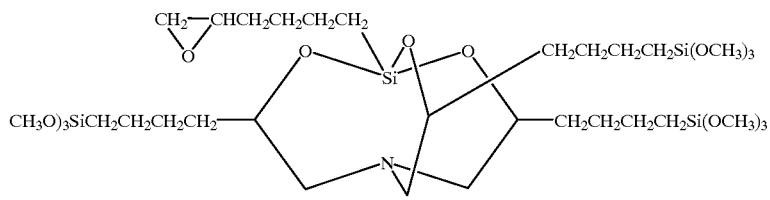
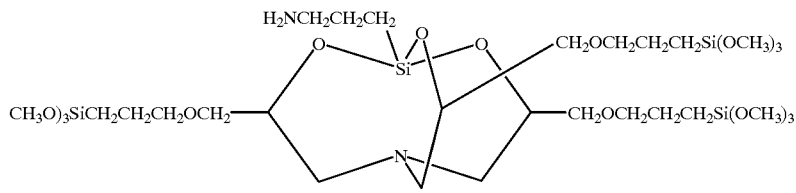
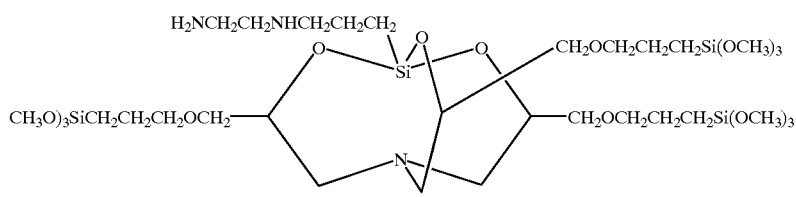
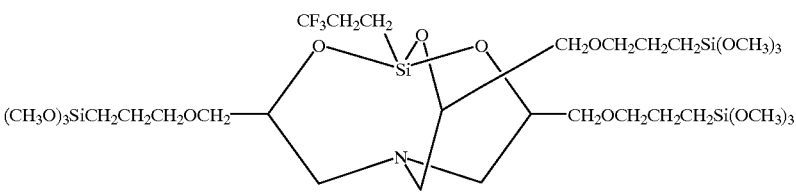
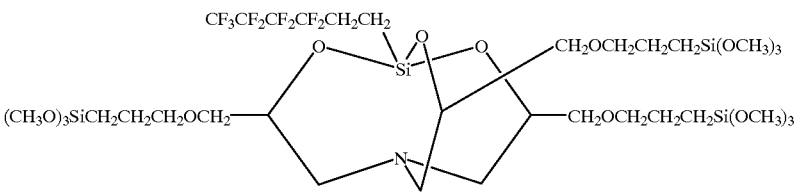
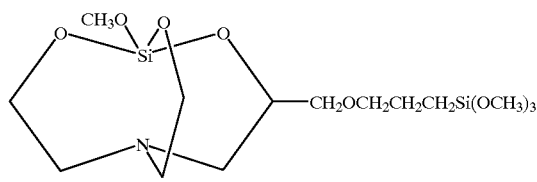
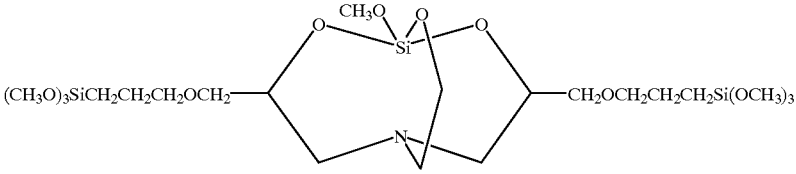

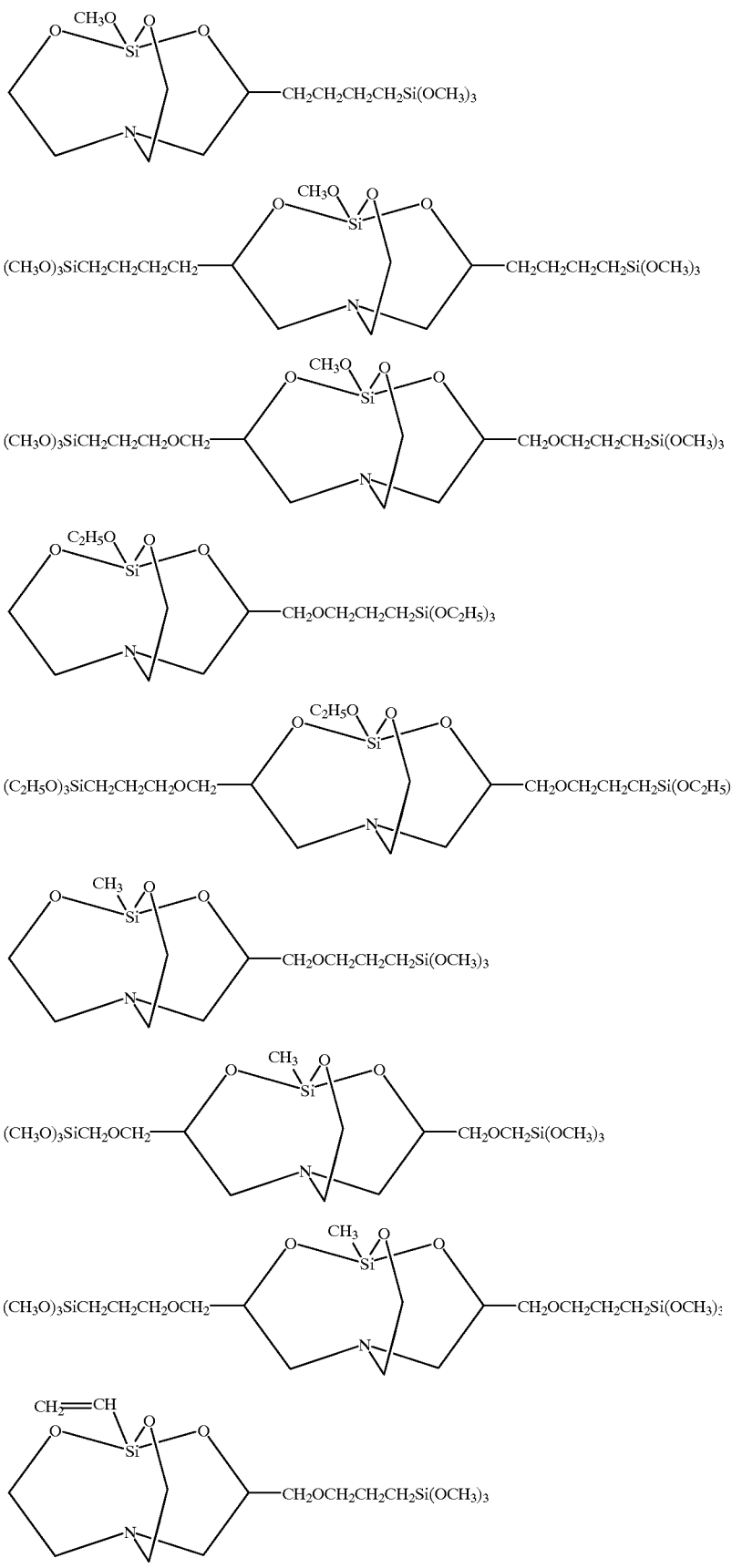

-continued
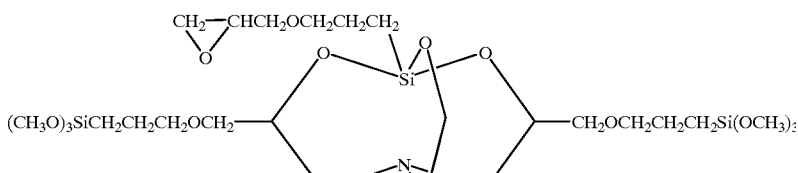

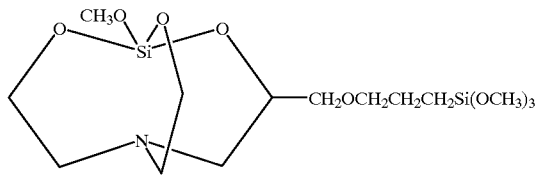

Examples of methods for manufacturing the silatrane derivative of the present invention include the following. The first method of preparing a silatrane derivative according to the present invention comprises reacting an epoxy group-containing trialkoxysilane compound having the formula:

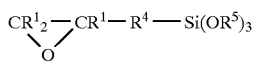

with a compound selected from the group consisting of ammonia and an amine compound having the formula:

—NH$_y$(CR$^1{}_2$CR$^1{}_2$OH)$_{(3-y)}$ wherein R$^1$, R$^4$, and R$^5$ are as defined above and y is 1 or 2. The first method produces a silatrane derivative containing a silicon-bonded glycidoxyalkyl group or oxiranylalkyl group.

The second method of preparing a silatrane derivative according to the present invention comprises reacting an epoxy group-containing alkoxysilane compound having the formula:

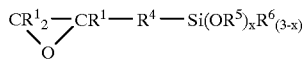

and an alkoxysilane compound having the formula:

with a compound selected from the group consisting of ammonia and an amine compound having the formula:

wherein R$^1$, R$^3$, R$^4$, R$^5$, and R$^6$ are as defined above; x is 1, 2, or 3; and y is 1 or 2.

With these methods, it is surmised that the ammonia or amine compound causes the epoxy groups to undergo a ring cleavage reaction, and the hydroxyl groups produced by this ring cleavage reaction, or the hydroxyl groups in the amine compound, undergo an alkoxy group exchange reaction with the alkoxy groups bonded to silicon atoms in the alkoxysilane, thus resulting in a cyclization reaction and forming the silatrane structure.

In the former manufacturing method, the epoxy group-containing trialkoxysilane compound is a raw material for forming the skeleton of the above-mentioned silatrane derivative, and it is also a raw material for introducing trialkoxysilyl groups into the molecules of the above-mentioned silatrane derivative. In the formula for the epoxy group-containing trialkoxysilane compound, R$^1$, R$^4$, and R$^5$ are as defined above. Examples of the epoxy group-containing trialkoxysilane compound include 4-oxiranylbutyltrimethoxysilane, 8-oxiranyloctyltrimethoxysilane, 3-glycidoxypropyltrimethoxysilane, 3-glycidoxypropyltriethoxysilane, glycidoxymethyltrimethoxysilane, and glycidoxymethyltriethoxysilane.

The ammonia or amine compound is a raw material for forming the skeleton of the silatrane derivative of the present invention. R$^1$ in the formula for the amine compound is as defined above and y is 1 or 2. Examples of this amine compound include 2-hydroxyethylamine, 2,2'-dihydroxyethylamine, and 2-hydroxy-2-methyl-ethylamine.

In the former manufacturing method, no limit is imposed on the amount of the epoxy group-containing trialkoxysilane compound added with respect to the ammonia, but in order to suppress the generation of by-products and obtain the silatrane derivative at a good yield, if the reaction is conducted under conditions where the ammonia is not lost by evaporation, then this epoxy group-containing trialkoxysilane compound should be used in an amount of 3 to 30 mol, and preferably 4 to 20 mol, per mole of ammonia. This means that it is recommended that this epoxy group-containing trialkoxysilane compound be used in the approximate stoichiometric amount or in an excess amount with respect to the ammonia in this manufacturing method. In general, the generation of by-products will be suppressed if the epoxy group-containing trialkoxysilane compound is used in an excess amount to the extent that the reaction does not slow down, but excess epoxy group-containing trialkoxysilane compound will remain behind. This unreacted epoxy group-containing trialkoxysilane compound that remains can be separated and recovered from the silatrane derivative by distillation or the like following the reaction. This reaction can also be conducted while ammonia gas is blown into the epoxy group-containing trialkoxysilane compound. When a reaction such as this is conducted in an open system, part of the ammonia will not react and will instead be released outside the system, so it must be used in an excess amount corresponding to this loss.

In the former manufacturing method, no limit is imposed on the amount of the epoxy group-containing trialkoxysilane compound added with respect to the amine compound, but in order to suppress the generation of by-products and obtain the silatrane derivative at a good yield, if y in this amine compound is 1, then this epoxy group-containing trialkoxysilane compound should be used in an amount of 1.5 to 10 mol, and preferably 2 to 5 mol, per mole of this amine compound, and if y in this amine compound is 2, then this epoxy group-containing trialkoxysilane compound should be used in an amount of 2.5 to 20 mol, and preferably 3 to 10 mol. This means that it is recommended that this epoxy group-containing trialkoxysilane compound be used in the approximate stoichiometric amount or in an excess amount with respect to the amine compound in this manufacturing method. In general, the generation of by-products will be suppressed if the epoxy group-containing trialkoxysilane compound is used in an excess amount to the extent that the reaction does not slow down, but excess epoxy group-containing trialkoxysilane compound will remain behind. This unreacted epoxy group-containing trialkoxysilane compound that remains can be separated and recovered from the silatrane derivative as needed by distillation or the like following the reaction.

In the latter manufacturing method, the epoxy group-containing alkoxysilane compound is a raw material for introducing alkoxysilyl groups into the molecules of the silatrane derivative. In the formula for the epoxy group-containing alkoxysilane compound, $R^1$, $R^4$, $R^5$, and $R^6$ are as previously defined and x is 1, 2, or 3, with 3 being preferable. Examples of this epoxy group-containing alkoxysilane compound include 4-oxiranylbutyltrimethoxysilane, 4-oxiranylbutylmethyldimethoxysilane, 8-oxiranyloctyltrimethoxysilane, 3-glycidoxypropyltrimethoxysilane, 3-glycidoxypropyltriethoxysilane, 3-glycidoxypropylmethyldimethoxysilane, 3-glycidoxypropylmethyldiethoxysilane, and glycidoxymethyltriethoxysilane.

In the latter manufacturing method, the ammonia or amine compound is a raw material for forming the skeleton of the silatrane derivative. In the formula for the amine compound $R^1$ is as defined above and y is 1 or 2. Examples of this amine compound are the same as the compounds listed above in the former method.

In the latter manufacturing method, the alkoxysilane compound is a raw material for forming the skeleton of the silatrane derivative. In the formula for the alkoxysilane compound $R^3$ and $R^5$ are as defined above. Examples of this alkoxysilane compound include tetramethoxysilane, tetraethoxysilane, methyltrimethoxysilane, methyltriethoxysilane, vinyltrimethoxysilane, vinyltriethoxysilane, phenyltrimethoxysilane, 3-methacryloxypropyltrimethoxysilane, 3,3,3-trifluoropropyltrimethoxysilane, nonafluorobutylethyltrimethoxysilane, 3-aminopropyltrimethoxysilane, 3-aminopropyltriethoxysilane, and N-(2-aminoethyl)-3-aminopropyltrimethoxysilane.

In the latter manufacturing method, no limit is imposed on the amounts of the epoxy group-containing alkoxysilane compound and alkoxysilane compound added with respect to the ammonia, but in order to suppress the generation of by-products and obtain the silatrane derivative at a good yield, if the reaction is conducted under conditions where the ammonia is not lost by evaporation, then the epoxy group-containing alkoxysilane compound should be used in an amount of 2 to 20 mol, and preferably 3 to 15 mol, per mole of ammonia. The alkoxysilane compound should be added in an amount of 0.5 to 50 mol per mole of ammonia, with a range of 1 to 20 mol being preferable. This means that it is recommended that the alkoxysilane compound be used in the approximate stoichiometric amount or in an excess amount with respect to the ammonia. In general, the generation of by-products will be suppressed if the alkoxysilane compound is used in an excess amount to the extent that the reaction does not slow down, but excess alkoxysilane compound will remain behind. This unreacted alkoxysilane compound that remains can be separated and recovered from the silatrane derivative by distillation or the like following the reaction. This reaction can also be conducted while ammonia gas is blown into a mixture of the epoxy group-containing alkoxysilane and the alkoxysilane compound and the alkoxysilane compound. When a reaction such as this is conducted in an open system, part of the ammonia will not react and will instead be released outside the system, so it must be used in an excess amount corresponding to this loss.

In the latter manufacturing method, no limit is imposed on the amounts of the epoxy group-containing alkoxysilane compound and the alkoxysilane compound added with respect to the amine compound, but in order to obtain the silatrane derivative at a good yield, if y in the amine compound is 1, then the epoxy group-containing alkoxysilane compound should be used in an amount of 0.5 to 10 mol, and preferably 0.8 to 5 mol, per mole of this amine compound, and if y in this amine compound is 2, then the epoxy group-containing alkoxysilane compound should be used in an amount of 1.5 to 20 mol, and preferably 1.8 to 10 mol, with an amount of about 2 mol being particularly favorable. The amount in which the alkoxysilane compound is added should be 0.5 to 50 mol, and preferably 1 to 20 mol, per mole of the amine compound. This means that it is recommended that the alkoxysilane compound be used in the approximate stoichiometric amount or in an excess amount with respect to the amine compound in this manufacturing method. In general, the generation of by-products will be suppressed if the alkoxysilane compound is used in an excess amount to the extent that the reaction does not slow down, but excess alkoxysilane compound will remain behind. This unreacted alkoxysilane compound that remains can be separated and recovered from the silatrane derivative as needed by distillation or the like following the reaction.

In the above methods for manufacturing a silatrane derivative, the reactions will proceed either at room temperature or under heating, but heating to 100° C. or lower is preferred in order to reduce the reaction time. The use of an organic solvent is optional, but examples of organic solvents that can be used include hexane, heptane, octane, and other such aliphatic hydrocarbons; toluene, xylene, and other such aromatic hydrocarbons; methanol, ethanol, isopropanol, and other such alcohols; acetone, methyl isobutyl ketone, and other such ketones; diethyl ether, tetrahydrofuran, and other such ethers; ethyl acetate, isoamyl acetate, and other such esters; and dimethylformamide, dimethylacetamide, and other such amide compounds. The use of an alcohol such as methanol or ethanol in particular will allow the reaction time to be shortened and the targeted silatrane derivative to be obtained at an even better yield. When an alcohol is added, it is preferable to use an alcohol that has the same number of carbons as the silicon atom-bonded alkoxy groups in the raw material epoxy group-containing trialkoxysilane compound or epoxy group-containing alkoxysilane compound and the alkoxysilane compound so that the alkoxy groups bonded to silicon atoms will undergo an alkoxy group exchange reaction during the above reaction. Also, when an alcohol is added, the reaction can be made markedly shorter, and the yield of the silatrane derivative that is obtained can be increased, by conducting the reaction at the reflux temperature of this alcohol.

The silatrane derivative of the present invention can be used, for example, to impart adhesive properties to silicone compositions cured by condensation reactions, silicone compositions cured by hydrosilylation reactions, silicone compositions cured by UV rays or other high-energy rays, and other such curable silicone compositions, as well as to alkoxysilane-modified polyether-based curable compositions, curable polyurethane resin and rubber compositions, curable epoxy resin compositions, curable polysulfide resin compositions, curable unsaturated polyester resin compositions, and other such curable compositions, or it can be used as a primer which increases the adhesion of the above-mentioned curable compositions when applied to the surface of a metal, glass, plastic, or other such substrate. The silatrane derivative is particularly useful with silicone compositions cured by condensation reactions, silicone compositions cured by hydrosilylation reactions, silicone compositions cured by UV rays or other high-energy rays, and other such curable silicone compositions.

The adhesion promoter of the present invention may be composed solely of the above-mentioned silatrane derivative, or of a mixture of this silatrane derivative with a known adhesion promoter or with a known organic solvent Examples of known adhesion promoters that can be used together with this silatrane derivative include methyltrimethoxysilane, vinyltrimethoxysilane, allyltrimethoxysilane, 3-methacryloxypropyltrimethoxysilane, 3-glycidoxypropyltrimethoxysilane, 3-aminopropyltrimethoxysilane, N-(2-aminoethyl)-3-aminopropyltrimethoxysilane, bis(trimethoxysilyl)propane, and bis(trimethoxysilyl)hexane. The amino group-containing alkoxysilane or epoxy compound remaining unreacted through the process of manufacturing this silatrane derivative, as well as any reaction products other than the silatrane derivative produced by this reaction, may be left mixed in the final product. In this case, the silatrane derivative content should be at least 10 wt %, with at least 50 wt % being preferable and at least 70 wt % being even better. The reason for this is that the adhesion promotion effect will tend to be diminished if the silatrane derivative content is below this range.

Silatranes can also be included in curable compositions. The curable silicone composition of the present invention will now be described in detail. The curable silicone composition of the present invention is characterized by containing the above-mentioned silatrane derivative. Examples of curable silicone compositions containing this derivative include condensation reaction-curable silicone compositions cured by a condensation reaction such as a dealcoholization condensation reaction, a dehydration condensation reaction, a dehydrogenation condensation reaction, a de-oxime condensation reaction, a de-acetic acid condensation reaction, or a de-acetone condensation reaction; silicone compositions cured by hydrosilylation reactions; and high-energy ray-curable silicone compositions cured by high-energy rays, such as in a mercapto-vinyl addition reaction, an acrylic functional group radical reaction, or a cationic polymerization reaction for epoxy groups or vinyl ether groups. A silicone composition cured by a hydrosilylation reaction is particularly favorable.

No limit is imposed on the blend amount of the silatrane derivative in the curable silicone composition of the present invention, but the silatrane derivative should be contained in an amount of 0.01 to 20 wt %, and preferably 0.05 to 10 wt %, in the curable silicone composition. A range of 0.1 to 5 wt % is particularly favorable.

EXAMPLES

The silatrane derivative and curable silicone composition of the present invention will now be described in further detail through practical examples.

Reference Example 1

31.5 g (0.3 mol) of 2,2'-dihydroxyethylamine, 91.3 g (0.6 mol) of tetramethoxysilane, and 70.9 g (0.3 mol) of 3-glycidoxypropyltrimethoxysilane were put into a 500 mL four-neck flask equipped with an agitator, a thermometer, and a reflux condenser. This system was heated and agitated for 100 hours at 50° C. Next, the entire amount of reaction mixture thus obtained was transferred to a pear-shaped flask, and the low-boiling component was distilled off by a rotary evaporator, which yielded 117.9 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced.

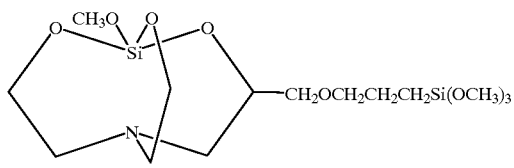

The content of this silatrane derivative was over 90 wt %. This transparent liquid was termed an adhesion promoter.

Reference Example 2

12.2 g (0.2 mol) of 2-hydroxyethylamine, 125.0 g (0.6 mol) of tetraethoxysilane, 111.4 g (0.4 mol) of 3-glycidoxypropyltriethoxysilane, and 30 g of ethanol were put into a 500 mL four-neck flask equipped with an agitator, a thermometer, and a reflux condenser. This system was heated and agitated for 15 hours at the ethanol reflux temperature. Next, the entire amount of reaction mixture thus obtained was transferred to a pear-shaped flask, and the low-boiling component was distilled off by a rotary evaporator, which yielded 134.5 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced.

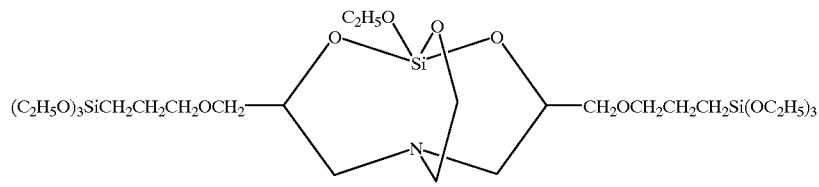

The content of this silatrane derivative was over 90 wt %. This transparent liquid was termed an adhesion promoter.

Reference Example 3

12.2 g (0.2 mol) of 2-hydroxyethylamine, 81.7 g (0.6 mol) of methyltrimethoxysilane, 94.5 g (0.4 mol) of 3-glycidoxypropyltrimethoxysilane, and 32 g of methanol were put into a 500 mL four-neck flask equipped with an agitator, a thermometer, and a reflux condenser. This system was heated and agitated for 8 hours at the methanol reflux temperature. Next, the entire amount of reaction mixture thus obtained was transferred to a pear-shaped flask, and the low-boiling component was distilled off by a rotary evaporator, which yielded 131.7 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced.

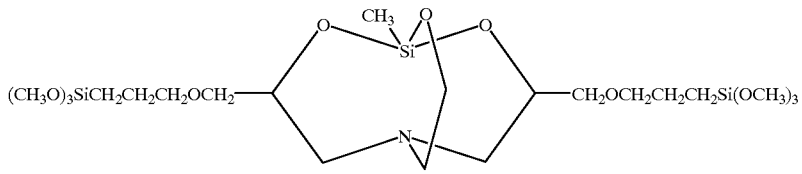

The content of this silatrane derivative was over 90 wt %. This transparent liquid was termed an adhesion promoter.

Reference Example 4

12.2 g (0.2 mol) of 2-hydroxyethylamine, 88.9 g (0.6 mol) of vinyltrimethoxysilane, 94.5 g (0.4 mol) of 3-glycidoxypropyltrimethoxysilane, and 32 g of methanol were put into a 500 mL four-neck flask equipped with an agitator, a thermometer, and a reflux condenser. This system was heated and agitated for 8 hours at the methanol reflux temperature. Next, the entire amount of reaction mixture thus obtained was transferred to a pear-shaped flask, and the low-boiling component was distilled off by a rotary evaporator, which yielded 132.8 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced.

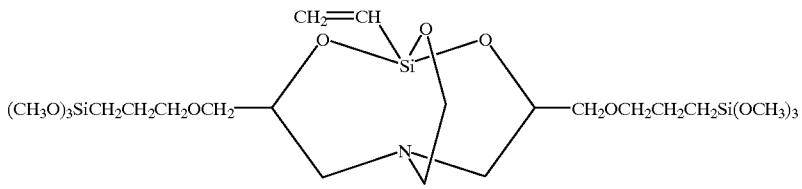

The content of this silatrane derivative was over 90 wt %. This transparent liquid was termed an adhesion promoter.

Reference Example 5

148.2 g (1.0 mol) of vinyltrimethoxysilane, 141.8 g (0.6 mol) of 3-glycidoxypropyltrimethoxysilane, and 64 g of methanol were put into a 500 mL four-neck flask equipped with an agitator, a thermometer, a gas introduction tube, and a reflux condenser. This system was heated and agitated at the methanol reflux temperature. Next, heating and reflux were continued for 24 hours while ammonia gas was blown into the reaction system for 2 minutes every hour at a flux of 50 mL/min. The entire amount of reaction mixture thus obtained was transferred to a pear-shaped flask, and the low-boiling component was distilled off by a rotary evaporator, which yielded 152.1 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced.

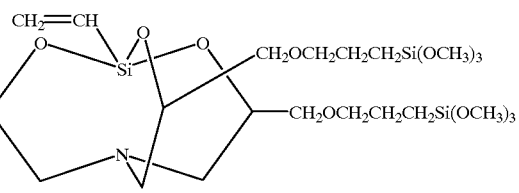

The content of this silatrane derivative was over 90 wt %. This transparent liquid was termed an adhesion promoter.

Reference Example 6

89.5 g (0.5 mol) of 3-aminopropyltrimethoxysilane and 236 g (1.0 mol) of 3-glycidoxypropyltrimethoxysilane were put into a 500 mL four-neck flask equipped with an agitator, and this system was agitated for 7 days at room temperature. The reaction mixture thus obtained was subjected to $^{29}$Si-nuclear magnetic resonance analysis and $^{13}$C-nuclear magnetic resonance analysis, which confirmed it to be a mixture composed of the raw materials 3-aminopropyltrimethoxysilane and 3-glycidoxypropyltrimethoxysilane and condensation products of these silanes. This reaction mixture was termed an adhesion promoter.

Reference Example 7

111 g (0.5 mol) of N-2-aminoethyl)-3-aminopropyltrimethoxysilane and 236 g (1.0 mol) of 3-glycidoxypropyltrimethoxysilane were put into a 500 mL four-neck flask equipped with an agitator, a thermometer, and a reflux condenser. This system was agitated for 114 hours at 50° C. The reaction mixture thus obtained was subjected to $^{29}$Si-nuclear magnetic resonance analysis and $^{13}$C-nuclear magnetic resonance analysis, which confirmed it to be a mixture composed of the raw materials N-(2-aminoethyl)-3-aminopropyltrimethoxysilane and 3-glycidoxypropyltrimethoxysilane and condensation products of these silanes. This reaction mixture was termed an adhesion promoter.

Examples 1 to 5 and Comparative Examples 1 to 3

A curable silicone composition was prepared as follows. A dimethylpolysiloxane terminated at both ends of the molecular chain with trimethoxysiloxy groups, fumed silica whose surface had been rendered hydrophobic by hexamethyldisilazane, methyltrimethoxysilane, and a titanium-based catalyst for use in a condensation reaction were uniformly mixed to prepare a de-alcoholization condensation reaction-curable silicone composition.

The adhesion promoters prepared in Reference Examples 1 to 7 were each blended in an amount of 0.5 wt % into this curable silicone composition to prepare seven types of curable silicone composition. For the sake of comparison, a curable silicone composition not containing any of these adhesion promoters was separately readied. These curable silicone compositions were used to coat the surfaces of the substrates shown in Table 1, after which the coatings were cured by being allowed to stand at room temperature for 7 days. The cured products thus obtained were in a rubbery form. The adhesion of the obtained eight types of silicone rubber with respect to the substrates was evaluated. Further, the silicone rubber was immersed in 50° C. hot water along with the substrate, after which the adhesion of the obtained eight types of silicone rubber to the substrate was also evaluated. The adhesion of the silicone rubber to the substrate was a given a "○" when the silicone rubber adhered well to a substrate, a "Δ" when the silicone rubber partially adhered to a substrate, and a "x" when the silicone rubber peeled completely away from the substrate. These evaluation results are given in Table 1.

TABLE 1

| | Present invention | | | | | Comparative examples | | |
|---|---|---|---|---|---|---|---|---|
| | 1 | 2 | 3 | 4 | 5 | 1 | 2 | 3 |
| Type of adhesion promoter | RE 1 | RE 2 | RE 3 | RE 4 | RE 5 | RE 6 | RE 7 | none |
| Initial adhesion of silicone rubber | | | | | | | | |
| Type of substrate | | | | | | | | |
| Aluminum | ○ | ○ | ○ | ○ | ○ | ○ | ○ | ○ |
| Stainless steel | ○ | ○ | ○ | ○ | ○ | ○ | ○ | Δ |
| Glass | ○ | ○ | ○ | ○ | ○ | ○ | Δ | ○ |
| Polycarbonate resin | ○ | ○ | ○ | ○ | ○ | ○ | ○ | ○ |
| Polybutylene terephthalate resin | ○ | ○ | ○ | ○ | ○ | Δ | Δ | x |
| Polyethylene terephthalate resin | ○ | ○ | ○ | ○ | ○ | Δ | ○ | Δ |
| Adhesion of silicone rubber after immersion in hot water | | | | | | | | |
| Type of substrate | | | | | | | | |
| Aluminum | ○ | ○ | ○ | ○ | ○ | Δ | ○ | Δ |
| Stainless steel | ○ | ○ | ○ | ○ | ○ | Δ | x | Δ |
| Glass | ○ | ○ | ○ | ○ | ○ | ○ | x | Δ |
| Polycarbonate resin | ○ | ○ | ○ | ○ | ○ | Δ | Δ | ○ |
| Polybutylene terephthaiate resin | ○ | ○ | ○ | ○ | ○ | Δ | x | x |
| Polyethylene terephthalate resin | ○ | ○ | ○ | ○ | ○ | Δ | Δ | Δ |

R.E = Reference Example

Practical Examples 6 to 10 and Comparative Examples 4 to 6

A curable silicone composition was prepared as follows. A dimethylpolysiloxane terminated at both ends of the molecular chain with dimethylvinylsiloxy groups, fumed silica whose surface had been rendered hydrophobic by hexamethyldisilazane, a dimethylsiloxane-methylhydrodienesiloxane copolymer terminated at both ends of the molecular chain with trimethylsiloxy groups, phenylbutynol, and a platinum-based catalyst for use in a hydrosilylation reaction were uniformly mixed to prepare a hydrosilylation reaction-curable silicone composition.

The adhesion promoters prepared in Reference Examples 1 to 7 were each blended in an amount of 1 wt % into this curable silicone composition to prepare seven types of curable silicone composition. For the sake of comparison, a curable silicone composition not containing any of these adhesion promoters was separately readied. These curable silicone compositions were used to coat the surfaces of the substrates shown in Table 2, after which the coatings were cured by being heated for 30 minutes in a 120° C. circulating hot air oven. The cured products thus obtained were in a rubbery form. The adhesion of the obtained eight types of silicone rubber with respect to the substrates was evaluated, with a "○" indicating that the silicone rubber adhered well to a substrate, a "Δ" that the silicone rubber partially adhered to a substrate, and a "x" that the silicone rubber peeled completely away from the substrate. These evaluation results are given in Table 2.

TABLE 2

|  | Present invention Examples | | | | | Comparative Examples | | |
| --- | --- | --- | --- | --- | --- | --- | --- | --- |
|  | 6 | 7 | 8 | 9 | 10 | 4 | 5 | 6 |
| Type of adhesion promoter | RE 1 | RE 2 | RE 3 | RE 4 | RE 5 | RE 6 | RE 7 | none |
| Initial adhesion of silicone rubber | | | | | | | | |
| Type of substrate | | | | | | | | |
| Aluminum | Δ | Δ | Δ | ○ | ○ | × | DNC | × |
| Stainless steel | Δ | Δ | Δ | ○ | ○ | × | DNC | × |
| Glass | Δ | ○ | ○ | ○ | ○ | Δ | DNC | × |
| Polycarbonate resin | × | ○ | Δ | ○ | ○ | × | DNC | × |
| Polybutylene terephthalate resin | × | Δ | Δ | ○ | ○ | × | DNC | × |

TABLE 2-continued

|  | Present invention Examples | | | | | Comparative Examples | | |
| --- | --- | --- | --- | --- | --- | --- | --- | --- |
|  | 6 | 7 | 8 | 9 | 10 | 4 | 5 | 6 |
| Polyethylene terephthalate resin | × | × | × | ○ | ○ | × | DNC | × |

DNC: did not cure; RE: Reference Example

Example 11

68.1 g (0.5 mol) of tetramethoxysilane, 70.9 g (0.3 mol) of 3-glycidoxypropyltrimethoxysilane, and 200 mL of a methanol solution of 2 M ammonia were put into a 500 mL autoclave and heated for 2 hours at 60° C. The entire amount of reaction mixture thus obtained was transferred to a pear-shaped flask and condensed under reduced pressure by a rotary evaporator, which yielded 73.9 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced, and that the content thereof was at least 70 wt %,

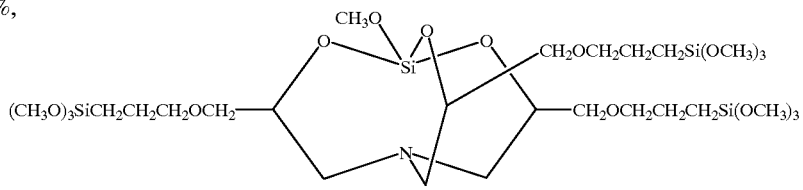

Example 12

136.2 g (1.0 mol) of methyltrimethoxysilane, 141.8 g (0.6 mol) of 3-glycidoxypropyltrimethoxysilane, and 64 g of methanol were put into a 500 mL four-neck flask equipped with an agitator, a thermometer, and a reflux condenser. This system was heated and refluxed under agitation. Heating and reflux were continued for 24 hours while ammonia gas was blown into the reaction solution for 2 minutes every hour at a flux of 50 mL/min. The entire amount of reaction mixture thus obtained was transferred to a pear-shaped flask and condensed under reduced pressure by a rotary evaporator, which yielded 150.5 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced, and that the content thereof was at least 70 wt %.

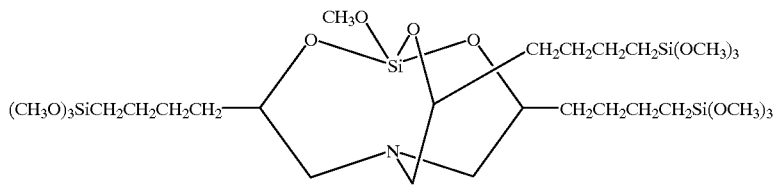

Example 13

118.2 g (0.5 mol) of 3-glycidoxypropyltrimethoxysilane and 30 g of methanol were put into a 300 mL four-neck flask equipped with an agitator, a thermometer, and a reflux condenser. This system was heated and refluxed under agitation. Heating and reflux were continued for 24 hours while ammonia gas was blown into the reaction solution for 2 minutes every hour at a flux of 50 mL/min. The entire amount of reaction mixture thus obtained was transferred to a pear-shaped flask and condensed under reduced pressure by a rotary evaporator, which yielded 86.4 g of a faintly yellow transparent liquid. This transparent liquid was subjected to $^{29}$Si-nuclear magnetic resonance analysis, and two signals attributable to the silicon atoms in the silane rings in two types of stereoisomer were observed at −68.0 ppm and −69.7 ppm, which confirmed that the silatrane derivative expressed by the following formula had been produced, and that the content thereof was at least 50 wt %.

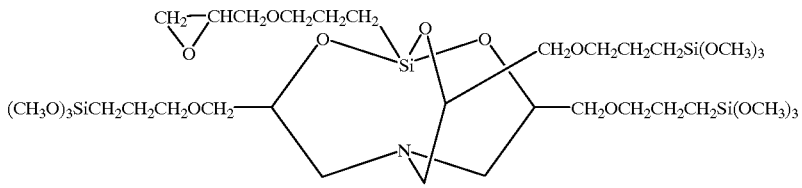

That which is claimed is:

1. A silatrane derivative having the formula:

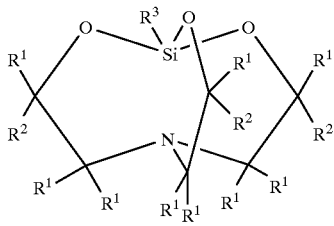

wherein each $R^1$ is independently a hydrogen atom or an alkyl group; each $R^2$ is independently selected from the group consisting of a hydrogen atom, an alkyl group, and an alkoxysilyl-containing organic group having the general formula:

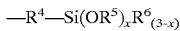

wherein $R^4$ is a divalent organic group, $R^5$ is a $C_1$ to $C_{10}$ alkyl group, $R^6$ is a monovalent hydrocarbon group, and x is 1, 2, or 3, with the proviso that at least one $R^2$ is the alkoxysilyl-containing organic group; and each $R^3$ is independently selected from the group consisting of a monovalent hydrocarbon group, a $C_1$ to $C_{10}$ alkoxy group, a glycidoxyalkyl group, an oxiranylalkyl group, an acyloxyalkyl group, a haloalkyl group, and an aminoalkyl group.

2. The silatrane derivative according to claim 1, wherein $R^1$ is a hydrogen atom or a methyl group; $R^4$ is valent organic group selected from the group consisting of ethylene, propylene, butylene, methyleneoxypropylene, and methyleneoxypentylene; $R^5$ is methyl or ethyl; $R^6$ is methyl; and x is 3.

3. A method of preparing a silatrane derivative, said method comprising the step of reacting (i) an epoxy group-containing trialkoxysilane compound having the formula:

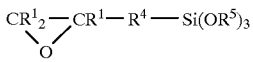

with (ii) a compound selected from the group consisting of ammonia and an amine compound having the formula:

wherein each $R^1$ is independently a hydrogen atom or an alkyl group, $R^4$ is a divalent organic group, $R^5$ is a $C_1$ to $C_{10}$ alkyl group, and y is 1 or 2.

4. The method according to claim 3, wherein the epoxy group-containing trialkoxysilane compound is used in at least about a stoichiometric amount relative to compound (ii).

5. The method according to claim 4, wherein compound (ii) is ammonia and the epoxy group-containing trialkyxysi-lane compound is used in an amount from 4 to 20 mole per mole of the ammonia.

6. The method according to claim 4, wherein compound (ii) is an amine, y is 1, and the epoxy group-containing trialkoxysilane compound is used in an amount from 2 to 5 moles per mole of the amine compound.

7. The method according to claim 4, wherein compound (ii) is an amine, y is 2, and the epoxy group-containing trialkoxysilane compound is used in an amount from 3 to 10 moles per mole of the amine compound.

8. The method according to claim 4, wherein the epoxy group-containing trialkoxysilane compound is used in a stoichiometric excess with respect to compound (ii), said method further comprising the step of separating the unreacted epoxy group-containing trialkoxysilane compound from the silatrane derivative.

9. The method according to claim 3, wherein the reaction is carried out at a temperature not greater than 100° C.

10. The method according to claim 3, wherein the reaction is carried out in the presence of an alcohol having the same number of carbon atoms as $R^5$ in compound (i).

11. A method of preparing a silatrane derivative, said method comprising the step of reacting (i) an epoxy group-containing alkoxysilane compound having the formula:

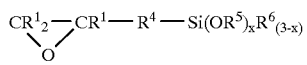

and (ii) an alkoxysilane compound having the formula:

with (iii) a compound selected from the group consisting of ammonia and an amine compound having the formula:

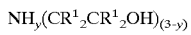

wherein each $R^1$ is independently a hydrogen atom or an alkyl group; each $R^3$ is independently selected from the group consisting of a monovalent hydrocarbon group, a $C_1$ to $C_{10}$ alkoxy group, a glycidoxyalkyl group, an oxiranyla-lkyl group, an acyloxyalkyl group, a haloalkyl group, and an aminoalkyl group; $R^4$ is a divalent organic group; $R^5$ is a $C_1$ to $C_{10}$ alkyl group; $R^6$ is a monovalent hydrocarbon group; x is 1, 2, or 3; and y is 1 or 2.

12. The method according to claim 11, wherein compound (iii) is ammonia and the epoxy group-containing alkoxysi-lane compound is used in an amount from 3 to 15 moles per mole of the ammonia.

13. The method according claim 11, wherein compound (iii) is an amine, y is 1, and the epoxy group-containing alkoxysilane compound is used in an amount from 0.8 to 5 moles per mole of the amine compound.

14. The method according to claim 11, wherein compound (iii) is an amine, y is 2, and the epoxy group-containing alkoxysilane compound is used in an amount from 1.8 to 10 moles per mole of the amine compound.

15. The method according to claim 11, wherein the alkoxysilane compound is used in at least about a stoichiometric amount relative to compound (iii).

16. The method according to claim 15, wherein compound (iii) is ammonia and the alkoxysilane compound is used in an amount from 1 to 20 moles per mole of the ammonia.

17. The method according to claim 15, wherein compound (iii) is an amine and the alkoxysilane compound is used in an amount from 1 to 20 moles per mole of the amine compound.

18. The method according to claim 15, wherein the alkoxysilane compound is used in a stoichiometric excess with respect to compound (iii), said method further comprising the step of separating the unreacted alkoxysilane compound from the silatrane derivative.

19. The method according to claim 11, wherein the reaction is carried out at a temperature not greater than 100° C.

20. The method according to claim 11, wherein the reaction is carried out in the presence of an alcohol, wherein the alcohol and $R^5$ in compound (i) and $R^5$ in compound (ii) each have the same number of carbon atoms.

21. An adhesion promoter comprising the silatrane derivative of claim 1 and an alkoxysilane-containing adhesion promoter.

22. A curable silicon composition comprising the silatrane derivative of claim 1.

23. The composition according to claim 22, wherein the curable silicone composition is curable by a hydrosilylation reaction.

24. The composition according to claim 22, wherein the silatrane derivative is present in an amount from 0.05 to 10 weight percent based on the total weight of the composition.

* * * * *